United States Patent
Tippet et al.

(10) Patent No.: US 9,650,313 B2
(45) Date of Patent: *May 16, 2017

(54) DEPOLYMERIZATION OF PLASTIC MATERIALS

(71) Applicant: FINA TECHNOLOGY, INC., Houston, TX (US)

(72) Inventors: Jon Tippet, League City, TX (US); James Butler, Spicewood, TX (US); James Assef, Pearland, TX (US); John Ashbaugh, Houston, TX (US); Jason Clark, Houston, TX (US); Michel Duc, Pau (FR); Jean-Bernard Cary, Le Havre (FR)

(73) Assignee: Fina Technology, Inc., Houston, TX (US)

( * ) Notice: Subject to any disclaimer, the term of this patent is extended or adjusted under 35 U.S.C. 154(b) by 207 days.

This patent is subject to a terminal disclaimer.

(21) Appl. No.: 14/586,521

(22) Filed: Dec. 30, 2014

(65) Prior Publication Data

US 2015/0210611 A1    Jul. 30, 2015

Related U.S. Application Data

(63) Continuation of application No. 13/247,285, filed on Sep. 28, 2011, now Pat. No. 8,969,638.

(60) Provisional application No. 61/409,145, filed on Nov. 2, 2010.

(51) Int. Cl.
| | |
|---|---|
| *C07C 1/00* | (2006.01) |
| *C07C 4/22* | (2006.01) |
| *B01J 8/06* | (2006.01) |
| *C08J 11/18* | (2006.01) |

(52) U.S. Cl.
CPC ............ *C07C 4/22* (2013.01); *B01J 8/062* (2013.01); *C08J 11/18* (2013.01); *C07C 2523/04* (2013.01); *C08J 2325/06* (2013.01); *Y02W 30/706* (2015.05)

(58) Field of Classification Search
CPC .................................................. B01J 8/062
USPC ........................................................ 585/241
See application file for complete search history.

(56) References Cited

U.S. PATENT DOCUMENTS

| | | | | |
|---|---|---|---|---|
| 5,406,010 | A * | 4/1995 | Ponsford | C07C 4/22 585/240 |
| 5,672,794 | A * | 9/1997 | Northemann | C07C 4/22 585/240 |
| 6,031,142 | A * | 2/2000 | Ponsford | C07C 4/22 585/241 |
| 7,626,062 | B2 * | 12/2009 | Carner | C10G 1/10 208/106 |

(Continued)

OTHER PUBLICATIONS

Z. Zhang, et al., "Chemical Recycling of Waste Polystyrene into Styrene over Solid Acids and Bases", Ind. Eng. Chem. Res., 34, pp. 4514-4519 (1995).

*Primary Examiner* — Nina Bhat
(74) *Attorney, Agent, or Firm* — Albert Shung

(57) ABSTRACT

A styrene monomer reclamation process and system is described. The styrene monomer reclamation process includes providing a waste plastic. The waste plastic includes styrenic polymers. The waste plastic is formed into polymer particles. At least a portion of the polymer particles are dissolved in a solvent to form a polymer stream. The dissolved polymer particles are depolymerized to form a styrene monomer stream.

18 Claims, 6 Drawing Sheets

(56) References Cited

U.S. PATENT DOCUMENTS 8,969,638 B2 * 3/2015 Tippet ..................... B01J 8/062
201/25

* cited by examiner

DEPOLYMERIZATION OF PLASTIC MATERIALS

CROSS-REFERENCE TO RELATED APPLICATIONS

This application is a continuation of U.S. patent application Ser. No. 13/247,285, filed on Sep. 28, 2011, which is a Non-Provisional of U.S. Provisional Patent Application No. 61/409,145 filed on Nov. 2, 2010.

FIELD

Embodiments of the present disclosure generally relate to depolymerization of waste materials, such as plastic materials. Specifically, these embodiments relate to the depolymerization of polystyrene and styrenic polymers

BACKGROUND

Waste plastic materials can be derived from post-consumer and post-industrial sources from around the world. The waste plastic may include any composition of plastic materials available from waste processors, for example. Before recycling, plastics are generally sorted according to their resin identification code, a method of categorization of polymer types. For example, high density polyethylene has a resin identification code of 2, while polystyrene has a resin identification code of 6, for example. Upon sorting, the plastics may be baled. Approximately 10% of the post-consumer plastic waste generated is composed of styrenic polymers, including polystyrene.

Traditional processes for reclaiming styrenic polymer waste are often unprofitable and hard to scale to commercial size. As a result, styrenic polymer waste is often mixed with other non-sorted waste plastics through mechanical recycling or used for energy recovery, despite modern automated sorting equipments that allows isolation of streams with greater than 90% wt pure styrenic polymers. Currently, little to no polystyrene is recycled from plastic bales in the United States. Mechanically sorted bales containing high amounts of waste polystyrene are often land filled or shipped to China for hand sorting to remove non-sytrenic polymer waste material for recycling. Further, traditional styrenic polymer reclamation processes are limited to producing reclaimed plastics that do not come into contact with food.

What is needed is a process for reclaiming styrenic polymer waste in a cost-efficient manner, whereby the process can be scaled to commercial size. Further, what is needed is a process that can produce reclaimed styrenic polymers capable of use with food products.

SUMMARY

Embodiments of the present disclosure include processes for the reclamation of styrenic polymer waste materials.

In one embodiment of the present disclosure, a styrene monomer reclamation process is disclosed. The styrene monomer reclamation process includes providing a waste plastic. The waste plastic includes styrenic polymers. The waste plastic is formed into polymer particles. At least a portion of the polymer particles are dissolved in a solvent to form a polymer stream. The dissolved polymer particles are depolymerized to form a styrene monomer stream.

In another embodiment of the present disclosure, a styrene monomer reclamation process is disclosed. The process includes providing a waste plastic; the waste plastic includes a styrenic polymer. The waste plastic is formed into polymer particles. The polymer particles include high density particles and low density particles. The high density polymers are separated from the low density particles. The low density particles are then removed from the polymer particles. At least a portion of the polymer particles are dissolved in a solvent to form a polymer stream. The solvent is toluene. The insoluble polymer particles are separated from the polymer stream. The polymer steam is then caustic treated, hydrotreated, and heated to a temperature below the critical temperature of the polymer stream in a preheater. The dissolved polymer particles are depolymerized to form a styrene monomer stream and the styrene monomer stream is cooled by heating the polymer stream in the preheater. The styrene monomer stream is neutralized and separated into a concentrated toluene stream including at least 50% toluene, a fuel oil stream, and a concentrated styrene stream.

In still another embodiment of the present disclosure a reactor for depolymerizing a styrenic polymer is disclosed. The reactor includes a firebox with a top surface, a bottom surface, and a firebox interior. The reactor further includes a plurality of vertical tubes. The vertical tubes penetrate the top surface and bottom surface of the firebox and form a radiant cell. The reactor still further includes a plurality of injectors, wherein each injector is fluidically connected to a vertical tube, a superheated steam line, wherein the superheated steam line is fluidically connected to the injector, and a depolymerization feed line, wherein the depolymerization feed line is fluidically connected to the injector. The reactor also includes a fuel gas injector, wherein the fuel gas injector penetrates the top surface of the firebox and a burner, wherein the burner is coupled to the fuel gas injector and within the firebox interior. A fuel gas line is fluidically coupled to the fuel gas injector.

DETAILED DESCRIPTION

Introduction and Definitions

A detailed description will now be provided. Each of the appended claims defines a separate invention, which for infringement purposes is recognized as including equivalents to the various elements or limitations specified in the claims. Each of the embodiments will now be described in greater detail below, including specific embodiments, versions and examples. This disclosure is not limited to these specific embodiments, versions or examples, which are included to enable a person having ordinary skill in the art to make and use the subject matter of the claims when the disclosure of this patent is combined with available information and technology.

Various terms as used herein are shown below. To the extent a term used in a claim is not defined below, it should be given the broadest definition skilled persons in the pertinent art have given that term as reflected in printed publications and issued patents at the time of filing. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Certain embodiments of the present disclosure are directed towards reclaiming polystyrene-rich plastic waste streams for conversion to styrenic polymers that are capable of use with food products. In these embodiments, polystyrene rich waste can be thermally depolymerized to highly pure styrene monomer. This styrene monomer may then be converted to styrenic polymers by conventional polymerization methods. Such processes may reduce the carbon footprint of styrene production by providing for the reuse of carbonaceous materials. Styrene, also known as vinyl benzene, is often polymerized to form polystyrene, acrylonitrile butadiene styrene (ABS), styrene-butadiene (SBS) rubber, styrene-butadiene latex, styrene-isoprene-styrene (SIS), styrene-ethylene/butylenes-styrene (S-EB-S), styrene-divinylbenzene (S-DVB), styrene-acrylonitrile resin (SAN) and unsaturated polyesters, for example. The formed polymers can be utilized in a variety of articles, such as insulation, fiberglass, pipes, vehicle parts, food containers and carpet backing, for example.

Certain embodiments of the present disclosure are comprised of four primary steps: preparation, dissolution, depolymerization, and purification. In other embodiments, the waste styrenic polymer preparation step may be omitted.

Preparation Process

Figure 1:
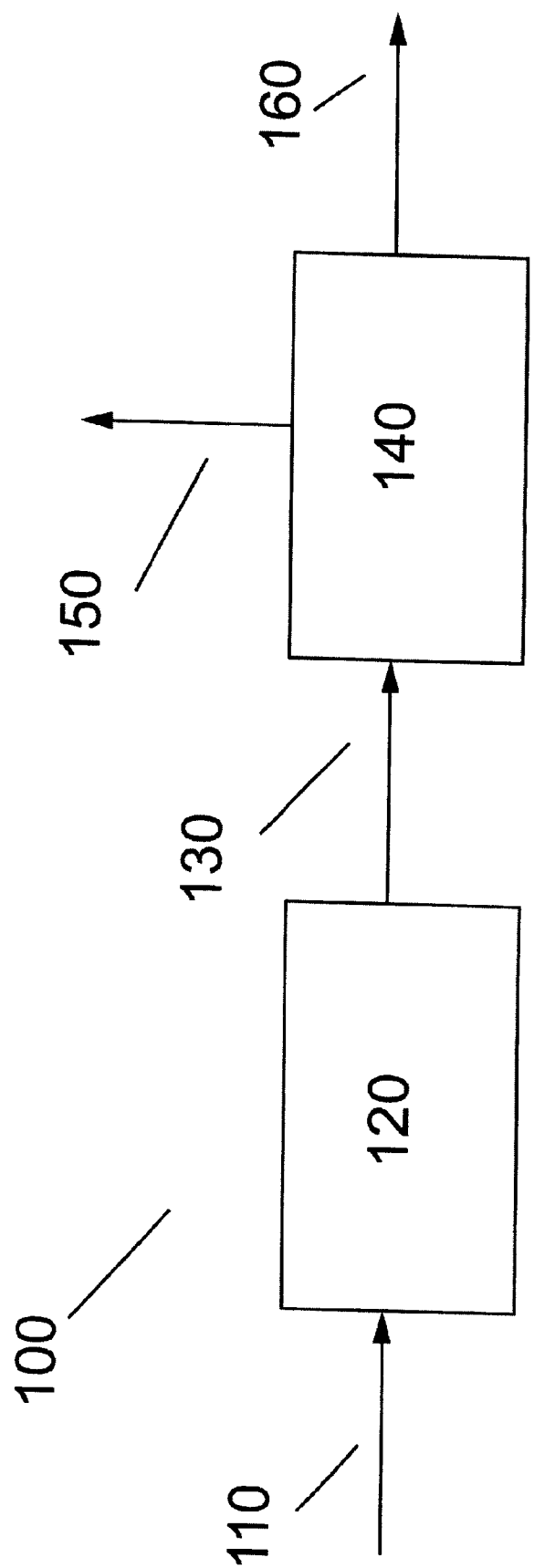
FIG. 1 is a block diagram of a preparation process consistent with the present disclosure.

In certain embodiments of the present disclosure, a styrenic polymer containing waste stream is prepared for dissolution. A non-limiting embodiment of a waste styrenic polymer preparation process 100 is illustrated in FIG. 1. Styrenic polymer containing waste steam 110 is provided to grinder 120. Grinder 120 reduces plastic waste of waste stream 110 into particles, which exit grinder 120 in particle stream 130. Such particles may vary in size but are generally of a size capable of handling within downstream processes. In certain embodiments, the particles may have a size of from about 3 mm to about 100 mm in diameter. As one of ordinary skill in the art with the benefit of this disclosure will recognize, grinder 120 may be any suitable apparatus for reducing the waste plastic to particle size.

In some embodiments of the present disclosure, particle stream 130 may be sent directly to the dissolution process (not shown). In other embodiments of the present disclosure, particle stream 130 is sent to separator 140. In separator 140, at least a portion of the non-styrenic polymer waste in particle stream 130 is separated from the styrenic polymer waste in particle stream 130. Separator 140 may include any process vessels capable of such separation. For example, the plastic materials may be separated via a variety or combination of float separators, density separators, electrostatic separators, density differential alteration separators, magnetic density separators or spectroscopic separators.

Spectroscopic separator typically use spectroscopic identification including, but not limited to near-infra-red, laser and x-ray to trigger a separation tool, such as an air puff. A mechanical conveyer may carry particle stream 130 under a spectroscopic sensor that identifies composition and placement of the plastic particle. The spectroscopic separator triggers the separation tool when the desired polymer is detected, separating the desired polymer from the rest of particle stream 130.

Float separators include, but are not limited to density separators and surface tension separators. Float separators may include float-sink separators, drum separators, and cyclone-media separators. In one or more embodiments of the present disclosure, separator 140 may include a float-sink separator. A float-sink separator may include a density bath of separation solution. The density of the separation solution may be adjusted to provide float-sink separation of the plastic materials. For example, the density of the separation solution is generally between the densities of the heavier and lighter plastic materials so that higher density components sink while lower density particles float.

In general, the density of unfilled polypropylene and polyethylene is less than 1.0 $g/cm^3$, while the density of ABS, High Impact Polystyrene (HIPS), filled polypropylene, SAN, PS, PC, polyvinylchloride (PVC) and nylon, for example, is greater than 1.0 $g/cm^3$. Thus, in one or more embodiments, the separation solution has a density of about 1.0 $g/cm^3$. In one or more embodiments, the separation solution includes water. In another embodiment, the separation solution includes an aqueous ionic salt solution.

It is further contemplated that the lighter plastic materials of particle stream 130 may include labels, which may include adhesive to adhere such to the plastic materials. While the labels and adhesive may float and separate from the heavier plastic materials, it is contemplated that the separation process may include chemical treatment thereof to assist in removal of such labels and adhesive. In one or more embodiments, the chemical treatment occurs in-situ with the separation.

In one or more embodiments, the chemical treatment includes caustic treatment. The caustic may be selected from sodium hydroxide, potassium hydroxide, sodium silicate, sodium carbonate, sodium metasilicate and combinations thereof, for example.

The caustic may be introduced to separator 140 at a rate sufficient to increase the alkalinity of the separation solution to a level sufficient to at least partially remove any adhesive from the plastic materials. In one or more embodiments, the caustic is introduced to separator 140 at a rate sufficient to provide a treated separation solution having a p-alkalinity of from about 0.3 to about 0.4, for example. In one or more embodiments, the caustic is introduced to separator 140 at a rate sufficient to increase the density of the separation solution. For example, the density may be increased to a density sufficient to separate polystyrene from the heavier plastic materials, such as a density greater than about 1.05 g/cc but less than about 1.15 g/cc, for example.

As described above, the separation solution may be introduced to separator 140 at a rate sufficient to increase the alkanity of the separation solution. Accordingly, the separation solution may be removed, introduced, recycled or combinations thereof at a rate corresponding to such desired alkalinity, density or combinations thereof.

In one or more embodiments, the separator 140 further includes a water wash. The water wash may be adapted to remove any caustic present in the plastic materials, to separate the lighter plastic materials from the heavier plastic materials, or a combination thereof, for example.

In one or more embodiments, separator 140 may include at least two separation steps. For example, the first step may be the treatment described above, while the second step may include density separation, such as that described herein. It is contemplated that the first separation step may separate heavier plastic materials, such as PVC, polylactic acid (PLA) and polyethylene terephalate (PET) from polystyrene, while the second step may be utilized to separate the polystyrene from the lighter plastic materials, such as polyolefins.

In certain embodiments, separator 140 has at least two outlet streams—light plastic materials stream 150 and dissolution inlet stream 160. In other embodiments, separator 140 may include three or more outlet streams, such as for instance, when multiple separation steps take place within separator 140 and the waste plastics are separated into multiple streams. Typically, light plastic stream 150 may include such materials as polyolefins and dissolution inlet stream 160 may include such materials as styrenic polymers. In one embodiment, light plastic stream 150 may include the "float" portion of particle stream 130, and the dissolution inlet stream may include the "sink" portion of particle stream 130, for instance, when a float-sink separator is used. It is contemplated that the light plastic materials stream 150 may be used, for instance, for clean fuel, recycled plastic article or cracker feed, depolymerized, further separated or further processed for subsequent use.

Dissolution Process

Figure 2:
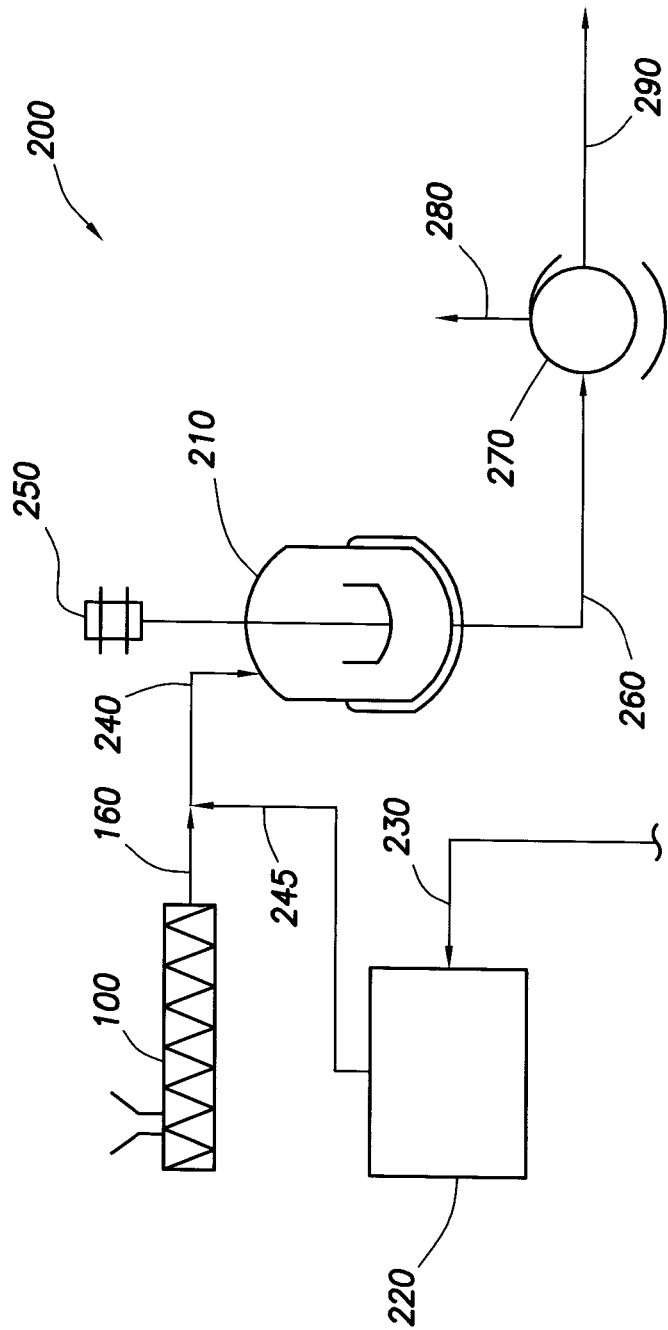
FIG. 2 is a schematic drawing of a dissolution process consistent with the present disclosure.

As shown in FIG. 2, dissolution inlet stream 160 may be transferred to a dissolution process 200. Dissolution inlet stream 160 generally includes polystyrene separated from lighter plastic materials in separator 140. It is further contemplated that dissolution inlet stream 160 may include plastic materials heavier than that of polystyrene. However, in one or more embodiments, such as that including a more than one separation step within separator 140, as discussed previously herein, it is contemplated that a majority of the heavier plastic materials, such as PVC, PLA and PET are not present in dissolution inlet stream 160 and are removed from separator 140 via another process stream (not shown).

In certain embodiments, dissolution process 200 may include dissolving tank 210, filter 270, and solvent storage tank 220. In other embodiments, dissolution process 200 may include only dissolving tank 210 and filter 270. In one embodiment of the present disclosure, the plastic material within dissolution inlet stream 160 may be contacted with a solvent by combining dissolution inlet stream 160 with solvent supply stream 245 to form dissolving tank inlet stream 240. Dissolving tank inlet stream 240 is then fed to dissolving tank 210. In another embodiment of the present disclosure (not shown), both dissolution inlet stream 160 and solvent supply stream 245 are input separately to dissolving tank 210 and dissolving tank inlet stream 240 is not formed.

Dissolving tank 210 may be any vessel suitable for mixing the solvent of solvent supply stream 240 and the plastic material within dissolution inlet stream 160. In one embodiment, dissolving tank 210 is equipped with stirrer 250. Stirrer 250 may be designed to agitate the plastic material and the solvent in dissolving tank 210 to improve mixing. In an alternative embodiment, dissolving tank 210 may be stirred by recirculating liquid through a pump exterior to the tank. Dissolving tank 210 may be operated either continuously, or in batch mode.

In some embodiments, it may be desirable to speed dissolution by increasing the temperature during the dissolution process. Suitable ways to increase the temperature during dissolution include, but are not limited to, heating the solvent in solvent supply stream 230 or heating the plastic material and solvent in dissolving tank 210, such as with a heating coil.

Dissolving tank outlet stream 260 may include a solution of solvent and dissolved plastic material together with insoluble material from dissolving tank 210. In certain embodiments, dissolving tank outlet stream 260 is input to filter 270.

In one or more embodiments, the insoluble materials are separated from the solution via filter 270. Filter 270 may be one or more filters, and may include such filters as rotary filters, fixed screens, filter presses or combinations thereof, for example. Filter 270 has two or more outlet streams. In certain embodiments, filter 270 has insolubles outlet stream 280 and dissolved plastic stream 290. In some embodiments, filter 270 is operated so as to minimize the amount of insoluble materials in dissolved plastic stream 290. In certain embodiments, the amount of insoluble materials in dissolved plastic stream 290 is less than 50% by weight. In other embodiments, the amount of insoluble materials in dissolved plastic stream 290 is less than 10% by weight. The insolubles may include insoluble polymers and inorganic salts such as talc, calcium carbonate filler or antimony oxide flame retardant.

The solvent may be removed from insolubles outlet stream 280 via known processes, such as distillation or steam stripping, for example. Insolubles outlet stream 280 may be utilized in subsequent processes, such as coking, for example.

When used as part of the dissolution process, solvent storage tank 220 may be used to store solvent. Solvent supply stream 245 is discharged from solvent storage tank 220. First side draw 450, which is an output stream from the purification process, may be an input stream to solvent storage tank 220. Solvent make up stream 230 may provide fresh solvent to solvent storage tank 220.

The solvent in solvent supply stream 230 may include any solvent capable of selectively dissolving polystyrene therein to form a solution. For example, the solvent may include an aromatic solvent, such as benzene, ethylbenzene, toluene, or mixtures thereof. In one embodiment, the solvent is toluene. In certain circumstances, it is possible to dissolve the waste plastic feedstock at room temperature in toluene. This approach may allow removal from the feed stream of most of the common non-styrenic plastics, such as PVC, PET, HDPE, LDPE and PP, which remain insoluble and are subsequently extracted by filtration. Some undesired fillers may also be extracted, as well as possible side-contaminants such as paper & cardboard or adhesives. The dissolving step of the present disclosure may result in the recovery of a purified styrenic polymer feedstock that may contain additives such as mineral or vegetable oils, metallic salts of fatty esters (e.g. zinc stearate), hexabromocyclododecane, and traces of primary & secondary antioxidants commonly used in styrenic plastics. The insolubles in toluene collected by filtration may be used as solid fuel for improving the energy balance of the styrenic polymer reclamation process.

The preparation and dissolution processes may provide a number of benefits to the styrenic polymer reclamation process. For instance, use of these processes may allow (i) selective extraction of many of the waste polystyrene contaminants present in waste steam 110 and (ii) minimize the viscosity of dissolved plastic stream 290, allowing a good atomization of the styrenic plastics to depolymerize and subsequently an optimal heat transfer in the depolymerization reactor (described below), which can provide high styrene monomer recovery yield.

Figure 4:
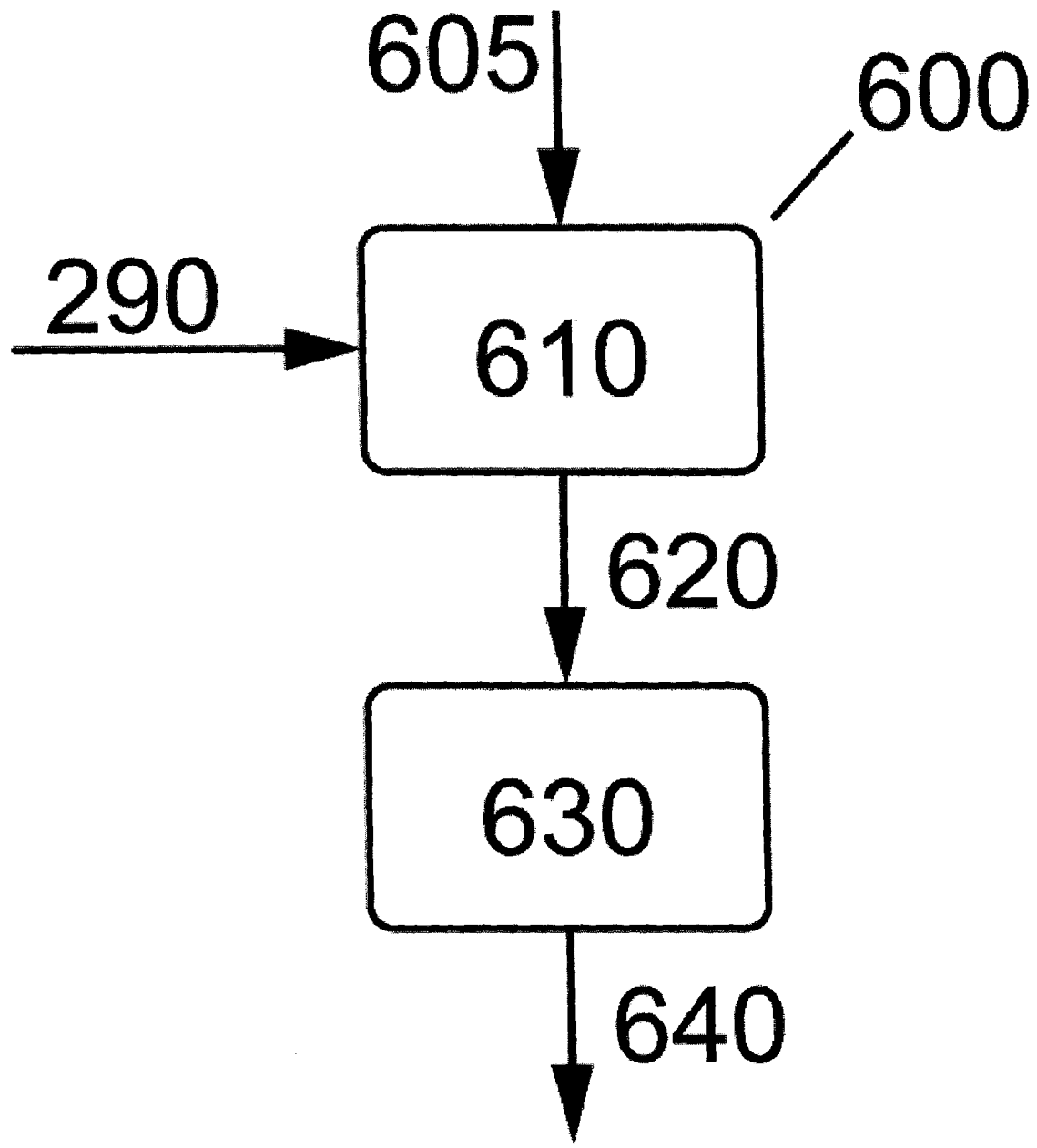
FIG. 4 is a block diagram of a caustic wash and hydrotreater consistent with the present disclosure.
Figure 5:
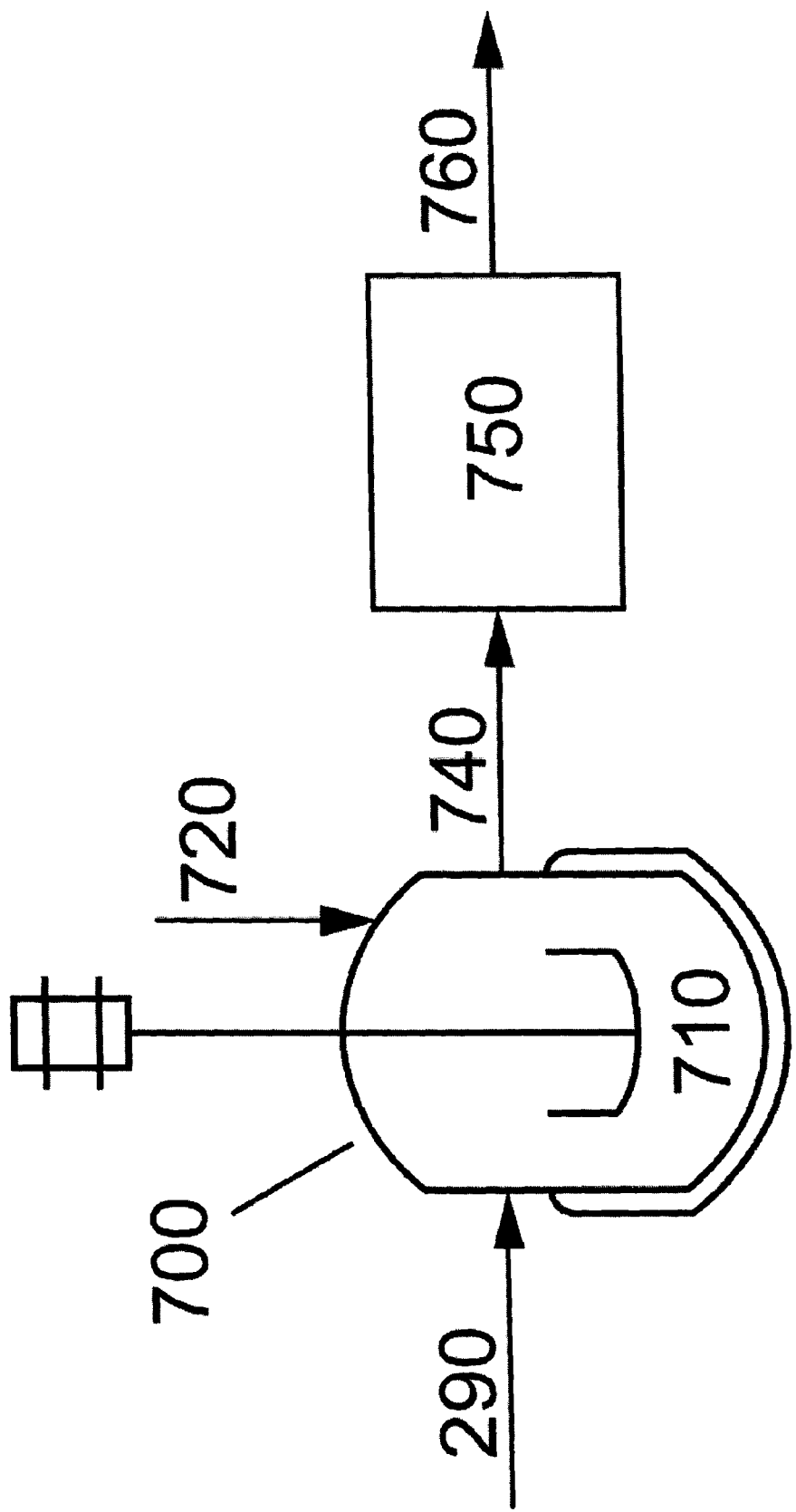
FIG. 5 is a block diagram of a hydrolysis process consistent with the present disclosure.

In other embodiments, dissolved plastic stream 290 may be fed to a caustic treatment, liquid phase hydrotreating, or both, as is shown in FIG. 4. In some embodiments of the present disclosure, dissolved plastic stream 290 may contain acrylonitrile containing polymer, such as ABS polymer (acrylonitrile butadiene styrene) and SAN polymer (styrene acrylonitrile). Nitrile groups may form undesirable cyanide gas during pyrolysis of the dissolved polymers. In these situations, it may be desirable to use caustic treatment 610 to remove the nitrile groups by treating with caustic. Caustic treatment of the nitrile groups in acrylonitrile polymers converts at least some of the nitrile groups to carboxylate groups. In such embodiments, dissolved plastic stream 290 is fed to caustic treatment 610. Caustic treatment stream 605 includes a caustic solution, such as potassium hydroxide or sodium hydroxide. In caustic treatment 610, the caustic solution and the dissolved plastics are contacted, resulting in a neutralization and reduction or removal of the nitrile groups. In addition, halides may be at least partially removed by the caustic treatment. In one non-limiting example, caustic treatment 610 is a counter current mixer. A phase transfer catalyst or crown ether may be used to facilitate the transfer of caustic into the organic phase to perform the treatment. In some embodiments, the phase transfer catalyst is recovered by regenerating the caustic and by washing it from the dissolved polymer solution.

Caustic treated dissolved plastic stream 620 is discharged from caustic treatment 610. Caustic treated dissolved plastic stream may be fed to liquid feed hydrotreater 630 or to preheater 310.

In some embodiments, dissolved plastic stream 290 may include halide containing polymers, polyvinylchloride or halide-containing flame retardants. In certain embodiments, a mild hydrotreating step may be used to remove the halogens from dissolved plastic stream 290 or caustic washed dissolved plastic stream 620. As shown in FIG. 4, caustic washed dissolved plastic stream 620 is fed to liquid phase hydrotreater 630. Liquid phase hydrotreater 630 serves to reduce or remove the halides from caustic washed dissolved plastic steam 620 with the use of traditional hydrotreating catalysts. After hydrotreatment, hydrotreated dissolved plastic stream 640 is fed to preheater 310.

Dissolved plastic stream 620 may be treated by caustic wash, hydrotreating, or both, depending on the impurities expected to be encountered. If both are used, in certain embodiments, nitrile removal by caustic wash is performed first as nitrogen may poison hydrotreating catalysts.

Depolymerization Process

Figure 3:
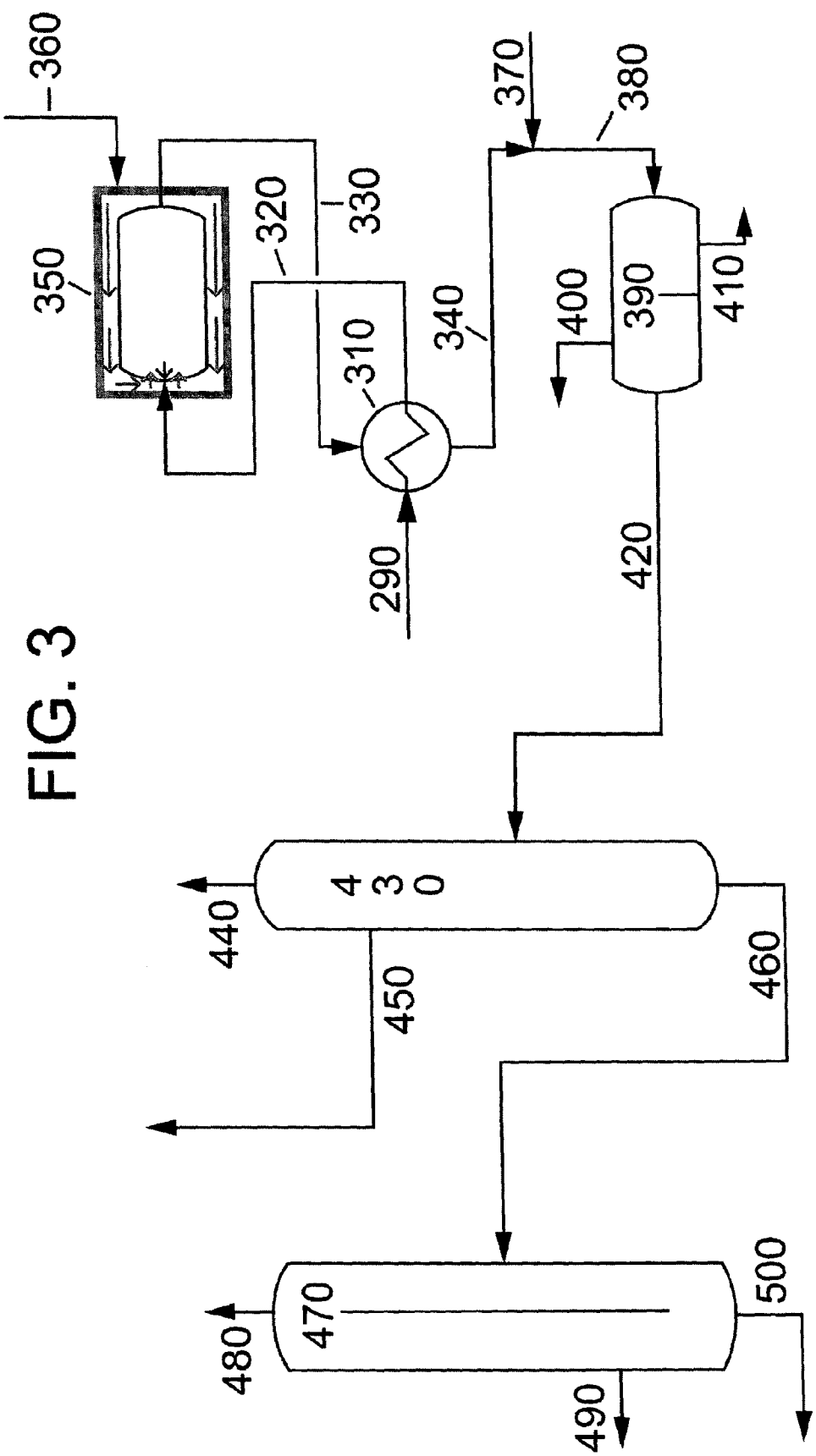
FIG. 3 is a schematic drawing of a depolymerization and purification process consistent with the present disclosure.

Dissolved plastic stream 290 is fed to depolymerization process 300 as shown in FIG. 3. As used herein, the term "depolymerize" is contemplated to mean end group scission from the polymer chain. Polymer degradation refers to processes adapted to cause random bond scission in the macromolecules of the polymer. Both modes of reaction can occur at the same time in the polymer chain.

Without being bound by theory, it is believed that above 300° C., end group scission predominates over random chain scission as desired for monomer formation. The end group chain scission yields styrene, the desired product. Random chain scission leads to by-products consisting for example of alpha-methylstyrene, 1,2-diphenylethane, stilbene and toluene.

In the depolymerization of styrenic polymers in certain embodiments of the present disclosure, the styrenic polymers are heated to the desired depolymerization temperature quickly. Slower heating may result in more random scission and a higher number of biphenyls. For instance, a near instant heating of the styrenic polymer to depolymerization temperatures, such a by laser, may result in a conversion of greater than 95% conversion to monomer. More typical conversion rates for reactors disclosed below is between 50 and 80% monomer. It is typically desirable to raise the temperature of the styrenic polymer to the desired depolymerization temperature in less than 3 seconds. In another embodiment, the time used to raise the styrenic polymer to the desired depolymerization temperature in the depolymerization reactor is less than one second.

The desired depolymerization should be sufficient to cause the depolymerization reaction to occur. As one of ordinary skill in the art in conjunction with this disclosure will recognize, the actual reactor temperature may depend on a number of factors including size and reactor configuration. In one or more embodiments, the reactor temperature of the reactor for depolymerization of styrenic polymers may be from a temperature of from about 330° C. and about 450° C., or from about 400° C. to about 800° C. or greater than or equal to about 600° C., as examples.

As shown in FIG. 3, in one or more embodiments, dissolved plastic stream 290 is heated prior to injection into depolymerization reactor 350. It has been found that in most cases, it is undesirable to boil the styrenic polymer solution in dissolved plastic stream 290. Generally, the temperature of dissolved plastic stream 290 should be kept below the critical temperature of the solvent. Temperatures above the critical temperature of the solvent may result in flashing of the solvent, precipitating the dissolved plastic and plugging of the equipment. Thus, when the solvent is toluene, the temperature should be kept below about 280° C. or about 240° C. when the pressure is approximately 600 psia and 318° C. at approximately 596 psia.

Dissolved plastic stream 290 may be heated by any appropriate means, as appreciated by one of skill in the art with the benefit of this disclosure. In certain embodiments, a heat exchanger may be used, such as preheater 310, as depicted in FIG. 3. In the embodiment shown in FIG. 3, dissolved plastic stream 290 is heated by reactor effluent 330. After dissolved plastic stream 290 is heated, it exits preheater 310 as depolymerization feed 320. Further, in the embodiment shown in FIG. 3, after cooling in preheater 310, cooled reactor effluent 340 exits preheater 310. Such heat integration, i.e., use of reactor effluent 330 to heat dissolved plastic stream 290 and dissolved plastic stream 290 to cool reactor effluent 330, allows for energy usage optimization of the styrenic polymer reclamation process.

Depolymerization reactor 350 may include any vessel capable of depolymerization of the dissolved styrenic polymer. For example, depolymerization reactor 350 may include an adiabatic fixed bed, fluidized bed, falling bed, tubular, or direct-fired tubular reactor. In one or more embodiments, the depolymerization reactor 350 includes fluid catalytic cracking technology.

In one embodiment of the present disclosure, such as is depicted in FIG. 3, depolymerization reactor 350 is a tubular reactor. Superheated steam stream 360 may further act to heat the styrenic polymer to pyrolysis temperature, typically 500 to 800° C., depending on the residence time within depolymerization reactor 350. Superheated steam stream 360 in the tubular reactor embodiments exceeds the reactor temperature of depolymerization reactor 350 In certain embodiments, the temperature of super heated steam stream is greater than 600°. In certain other embodiments, the temperature of super heated steam stream is greater than 700°. In still other embodiments, the temperature of super heated steam stream is greater than 800°. In certain embodiments, the steam-to-polymer solution mass flowrate ratio between about 0.1:1 to about 3:1 with high steam rates furnishing more of the heat from the steam.

In general, residence time of the styrenic polymer solution in depolymerization reactor 350 should be set as low as is possible. Longer residence times may result in more secondary reactions such as the conversion of styrene to ethyl benzene. In one embodiment, depolymerization reactor 350 is brought to about 600° C. for a residence time of less than or equal to 1 min. In another embodiment, the residence time in depolymerization reactor is less than or equal to 30 seconds.

In certain embodiments where depolymerization reactor 350 is a tubular reactor, depolymerization reactor 350 may be an empty tube. In other embodiments where depolymerization reactor 350 is a tubular reactor, depolymerization reactor 350 can be filled with static mixer elements. In still other embodiments where depolymerization reactor 350 is a tubular reactor, depolymerization reactor 350 can contain a loose packing of metal or silicon carbide beads in order to ease heat transport. Where depolymerization reactor 350 contains a loose packing of metal or silicon carbide beads, the packing can support some transition metal oxide catalysts, as those described in Ind. Eng. Chem. Res., 34, 4514 (1995), which is incorporated herein by reference. It has been determined that an empty tube or a tube with static mixers without any catalyst may minimize coke formation. In certain embodiment, potassium hydroxide may be co-injected with the depolymerization feed 320 to limit the risk of coke buildup in depolymerization reactor 350.

Figure 6:
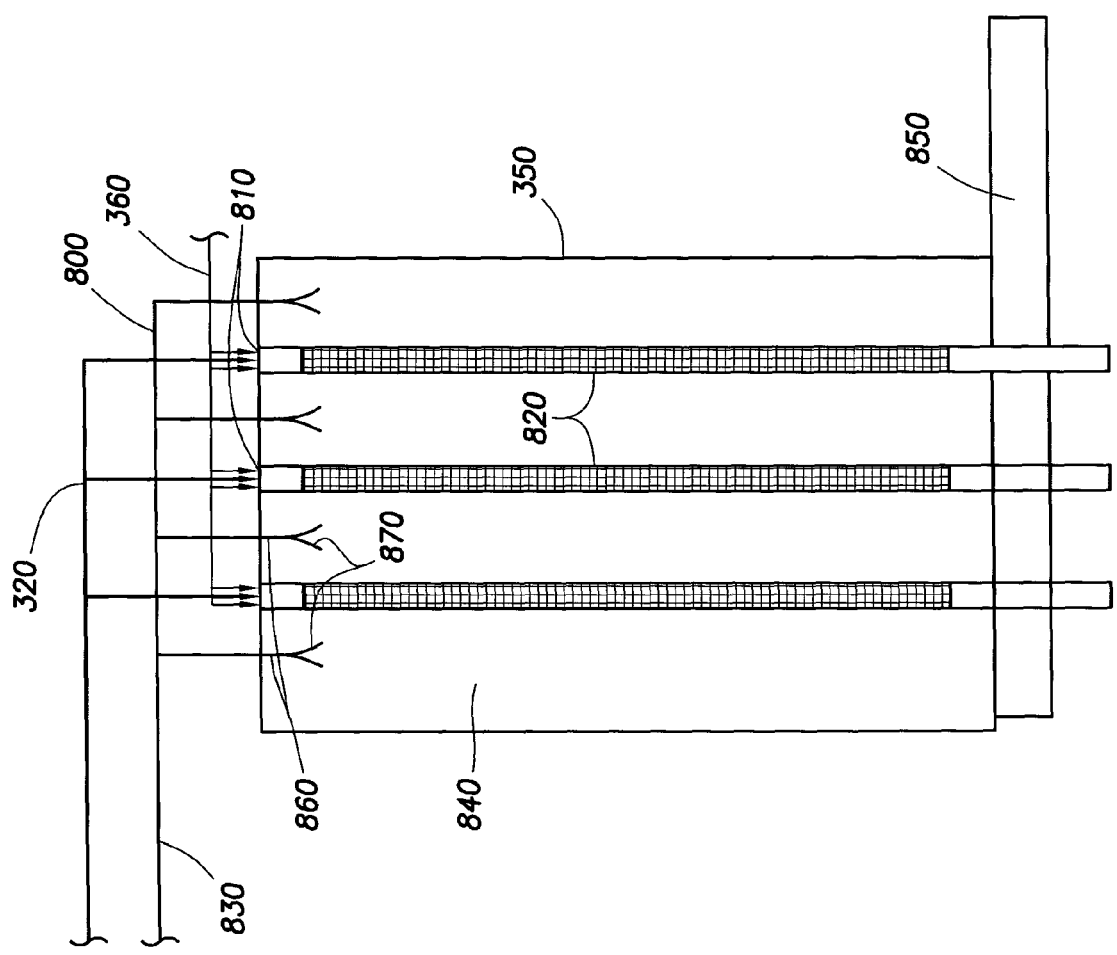
FIG. 6 is a schematic drawing of a directed heated multiple-tube reactor consistent with the present disclosure.

In another embodiment of the present disclosure, as shown in FIG. 6, depolymerization reactor 350 is a direct-heated multiple-tube reactor. When depolymerization reactor 350 is a direct-heated multiple-tube reactor, superheated steam stream is co-injected around injection nozzles 810 through which depolymerization feed 320 is injected into the reactor. Steam injection may serve to atomize the dissolved styrenic polymer in depolymerization feed 320. Steam injection may further mitigate coke formation in the reactor. The combined steam/dissolved styrenic polymer is transferred into tubes 820 that are arranged in rows, with rows of down-firing burners in-between. Typically, tubes 820 are less than 4" in diameter. In certain embodiments, a pig tail design with a pressure drop is used at the inlet to the tubes to evenly distribute the polymer solution between the tubes.

Tubes 820 in the direct-heated multiple tube reactor, like that of the tubular reactor, may be composed of stainless steel or Hastelloy C-276 or other suitable alloy. In certain embodiments where depolymerization reactor 350 is a direct-heated multiple-tube reactor, depolymerization reactor 350 may be an empty tube. In other embodiments where depolymerization reactor 350 is a direct-heated multiple-tube reactor, depolymerization reactor 350 can be filled with static mixer elements. In still other embodiments where depolymerization reactor 350 is a direct-heated multiple-tube reactor, depolymerization reactor 350 can contain a loose packing of metal beads in order to ease heat transport In certain embodiments of the present disclosure wherein direct-heated multiple tube reactors are used, fuel gas stream 830 is sprayed through fuel gas injectors 860 directly in the top-down burners 870 of firebox 840 enclosing parallel tubes 820 in rows forming a radiant cell. Tubes 820 penetrate the ceiling and the bottom of a radiant cell. Flue gas is drawn and evacuated through tunnels 850 arranged on the bottom of firebox 840. Firebox 840 may be equipped with dampers to hold a slight pressure therein. An outlet manifold system may collect the gaseous products of the direct-heated multiple tube reactor, which may then be conveyed through preheater 310 for heat recovery and preheating of depolymerization feed 320.

Direct heated multiple tube reactors may have certain advantages with respect to other depolymerization reactors. For instance, direct-heating technology combined with the reactor outlet heat recovery may allow reduction of the energy to drive the depolymerization reaction by as much as two thirds and may also allow reduction of the steam consumption required for the styrenic polymer waste depolymerization by as much as 75 to 85%.

Where depolymerization reactor 350 contains a loose packing of metal or silicon carbide beads, the packing can support certain catalysts that can improve thermal degradation during depolymerization. Examples of such catalyst include, but are not limited to transition metal oxide catalysts, such as those described in Ind. Eng. Chem. Res., 34, 4514 (1995), silica-aluminas, metal oxides, aluminas and zeolites, as examples. In one or more embodiments, the catalyst is supported on a metal or silicon carbide.

Additives are often incorporated into plastic materials to improve the properties thereof. Such additives may include, but are not limited to, antioxidants, heat stabilizers, UV stabilizers, flame retardants, antistatics, blowing agents, impact modifiers, compatibilizers, fillers, fiber reinforcements, fluorescent whiteners, pigments, organic colorants, carbon black, titanium dioxide, and lubricants, for example. Flame retardants can include brominated flame retardants, chlorinated flame retardants, antimony trioxide, phosphorous-containing flame retardants, aluminum hydroxide and boron-containing compounds, for example.

In certain embodiments, after cooling in preheater 310, cooled reactor effluent 340 may be fed to a water heat exchanger, allowing some low-pressure steam production and further cooling cooled reactor effluent 340. In some embodiments, after being fed to the water heat exchanger, cooled reactor effluent 340 may be passed through an aero-refrigerating tower, so as to recover some liquid water, liquid styrene oil and some residual non-condensed gases that can be used as gas fuel mixed with natural gas in the firebox burners or flared.

In some embodiments of the present disclosure, neutralizing solution stream 370 is combined with cooled reactor effluent 340 to form neutralized reactor effluent 380. Neutralizing stream includes a caustic or amine solution for neutralizing possible residual acid gases present in reactor effluent 340. Suitable non-limiting examples include sodium hydroxide and potassium hydroxide, although any suitable caustic solution may be used. Other examples include morpholine, diaminoethane and ethanol amine. The neutralizing solution is added at a rate to maintain the pH between 5 and 9.

In the embodiment depicted in FIG. 3, neutralized reactor effluent 380 is fed to compartment decanter 390. In compartment decanter 390, hydrocarbons from neutralized reactor effluent 380 are separated from steam condensate and salts from neutralization. Steam condensate is discharged from compartment decanter 390 in steam condensate stream 410. In certain embodiments of the present disclosure, light hydrocarbons may be present in neutralized effluent 380 and these may be discharged from compartment decanter 390 through decanter gas stream 400. Decanter gas stream 400 may in some embodiments be flared and in other embodiments may be recovered for fuel, depending on volume. Decanter product stream 420 is discharged from compartment decanter 390. Decanter product stream 420 may include styrene oil containing mostly aromatics including toluene, styrene monomer and higher aromatics. Decanter product stream 420 may also include benzene and toluene. Decanter product stream may also comprise high molecular weight hydrocarbons termed "tar." In some embodiments toluene, styrene monomer and higher aromatics comprise at least 60% wt of decanter product stream 420. In other embodiments, toluene, styrene monomer and higher aromatics comprise at least 70% wt of decanter product stream 420.

Purification Process

In certain embodiments of the present disclosure, the depolymerization process is closely coupled to an existing styrene manufacturing plant such that purification of the sytrenic monomer may be accomplished in whole or in part in separation equipment present in the existing styrene plant. In other embodiments of the present disclosure, such as for instance, where the styrene reclamation process is located separately from an existing styrene plant, it may be necessary to use additional equipment for purification of the styrene monomer. Purification of the styrenic monomer may be performed by traditional separation methods.

In one non-limiting embodiment of the present disclosure, benzene and toluene may be separated from the other hydrocarbon products in first distillation column 430. Decanter product stream may be fed to first distillation column 430. In some embodiments, first distillation column 430 is a steam column equipped with a steam-heated bottom exchanger. It has been found that first distillation column 430 operates efficiently under a partial vacuum, such as approximately 0.3 bar. First distillation column 430 may be operated to discharge three outlet streams: first overhead stream 440, first side draw 450, and first bottoms stream 460. First overhead stream 440 may be a concentrated benzene solution; in certain embodiments, first overhead stream 440 may contain more than 1% benzene. In other embodiments, first overhead stream 440 may contain more than 5% benzene.

In the non-limiting embodiment shown in FIG. 3, a concentrated toluene stream may be removed from first distillation column 430 as first side draw 450. First side draw 450 may comprise more than 90% toluene, with the remainder being mainly benzene and ethylbenzene. In certain other embodiments, first side draw 450 may comprise more than 93% toluene. First side draw 450 may be recirculated to preparation process 100, as described above. First bottoms stream 460 is concentrated in styrene monomer and higher aromatics.

The products can be separated according to known art for styrene production using a series of distillation columns operated under vacuum. In some embodiments, first bottoms stream 460 may be further refined. In other embodiments, first bottoms stream 460 may be used directly in a conventional GPPS, HiPS, SAN or ABS unit. In certain embodiments, such as the embodiment depicted in FIG. 3, first bottoms stream 460 may be further refined in a distillation column, such as secondary walled distillation column 470, which may be equipped with a steam-heated boiler. Secondary walled distillation column 470 may be operated at a lower pressure than first distillation column 430, such as at a pressure of around 0.05 bar. As shown in FIG. 3, secondary walled distillation column 470 may be operated to discharge two or three streams. For instance, secondary walled distillation column 470 may produce a second overhead stream 480, second side draw 490 and second bottoms stream 500. Second overhead steam 480 is typically concentrated in styrene monomer. Second overhead stream 480 may have less than 3% wt toluene and less than 0.2% wt of alpha methyl styrene. Secondary walled distillation column 470 may be operated with second side draw 490 when it is economical to produce a concentrated stream of alpha methyl styrene. Second side draw 490 may be omitted when it is not economical to produce a concentrated stream of alpha methyl styrene.

In another embodiment (not shown), first bottoms stream 460 may be fed to an ethyl benzene/styrene monomer distillation column ("BM/SM column") of a styrene monomer production unit. Before being injected into a BM/SM column, first bottoms stream 460 may being mixed with steam, such as steam from the BM/SM bottom Second bottoms stream 500 or the bottoms from the BM/SM column may contain mainly heavier aromatics, such as alpha methyl styrene that may be used in other chemical processes or used as fuel oil. In certain embodiments where depolymerization reactor 350 is a direct-heated multiple-tube reactor, second bottoms stream 500 may be used as fuel oil for the depolymerization reactor 350 burners. In such an embodiment, the depolymerization process may be auto-thermal or may generate a slight excess of energy. In certain embodiments of the present disclosure, styrene monomer recovery yield may be greater than 55% wt with respect to the polystyrene fraction of the polystyrene-rich plastic waste feedstock for the styrenic polymer reclamation process. In other embodiments of the present disclosure, styrene monomer recovery yield may be greater than 70% wt with respect to the polystyrene fraction of the polystyrene-rich plastic waste feedstock for the styrenic polymer reclamation process.

The resultant styrene monomer from the styrenic polymer reclamation process may be used as part of the styrene monomer feed stream of a conventional GPPS, HiPS, SAN or ABS unit. The clean styrene monomer produced by the styrenic polymer reclamation process may be used for the production of plastic food packagings.

It is expected that the processes of the present disclosure are capable of reducing the energy required for forming styrene monomer. For example, virgin styrene production processes (e.g., those forming styrene from ethylbenzene dehydrogenation) can require as much as 13,000 BTU/lb of styrene produced, while the process described herein may require less than 10,000 BTU/lb of styrene produced.

The following tables illustrate the expected energy savings from the processes described herein. However, the amount of energy needed to depolymerize PS in 1-7 bales is contingent on the following 3 factors: distance from the recycle source to the depolymerization plant; amount of PS in the waste plastic; and yield of styrene monomer during depolymerization. The 3 following tables detail the relationship of the variables.

The tables show that less energy will be used to produce styrene monomer from typical 1-7 bales with ~5% PS content than from fossil fuels. The further the depolymerization operation is from the recycle source, the greater the PS content may be to maintain energy savings.

TABLE 1

Amount of BTU/lb with recycle source within 100 miles.
Btu per lb of monomer with recycle within 100 miles.

| % PS in bail | 5% | 10% | 20% | 50% | 75% | 100% |
| --- | --- | --- | --- | --- | --- | --- |
| Total at 100% yield | 6325 | 5359 | 4887 | 4668 | 4798 | 4376 |
| 90% | 7028 | 5955 | 5430 | 5187 | 5331 | 4863 |
| 80% | 7907 | 6699 | 6108 | 5835 | 5997 | 5470 |
| 70% | 9036 | 7656 | 6981 | 6668 | 6854 | 6252 |
| 60% | 10542 | 8932 | 8144 | 7780 | 7996 | 7294 |
| 50% | 12651 | 10718 | 9773 | 9336 | 9595 | 8753 |

TABLE 2

Amount of BTU/lb with recycle source within 500 miles.
Btu per lb of monomer with recycle within 500 miles

| % PS in bail | 5% | 10% | 20% | 50% | 75% | 100% |
|---|---|---|---|---|---|---|
| Total at 100% yield | 14511 | 9679 | 7317 | 6223 | 6871 | 4765 |
| 90% | 16123 | 10755 | 8130 | 6915 | 7635 | 5295 |
| 80% | 18138 | 12099 | 9146 | 7779 | 8589 | 5956 |
| 70% | 20729 | 13827 | 10452 | 8890 | 9816 | 6807 |
| 60% | 24184 | 16132 | 12194 | 10372 | 11452 | 7942 |
| 50% | 29021 | 19358 | 14633 | 12446 | 13742 | 9530 |

TABLE 3

Amount of BTU/lb with recycle source within 1000 miles.
Btu per lb of monomer with recycle within 1000 miles

| % PS in bail | 5% | 10% | 20% | 50% | 75% | 100% |
|---|---|---|---|---|---|---|
| Total at 100% yield | 24742 | 15079 | 10354 | 8167 | 9463 | 5251 |
| 90% | 27491 | 16754 | 11505 | 9075 | 10515 | 5835 |
| 80% | 30928 | 18849 | 12943 | 10209 | 11829 | 6564 |
| 70% | 35346 | 21541 | 14792 | 11667 | 13519 | 7502 |
| 60% | 41237 | 25132 | 17257 | 13612 | 15772 | 8752 |
| 50% | 49484 | 30158 | 20708 | 16334 | 18926 | 10502 |

EXAMPLES

Example 1

A 1" O.D. single tube reactor was packed with a base layer of ¼" stainless steel balls and a small layer of potassium hydroxide on top of the balls. Reactor conditions were held as follows:

| Oil Feed Rate | Nitrogen Carrier Gas Flow | Water Rate 2 Molar Based on Toluene | Preheat Furnace Zones ° C. | Cat Bed Temp ° C. | Outlet Pressure (psig) | Polystyrene in Toluene | Reactor Pressure |
|---|---|---|---|---|---|---|---|
| ~2.6 g/min | 300 ml/min | 0.9 ml/min | 650 | 600 | 25 | 10 wt % | 1.7 bar |

After 11 days, no pressure drop across the reactor was observable. Styrene monomer in the reactor outlet was approximately 6.9%. Styrene yield varied but held between 65% and 70%. Heavies yield also held at between 15% and 20%. AMS and ethylene benzene concentrations increased over the 11 days, from a low for AMS of approximately 3.% at the beginning to approximately 3.5% at the end of the 11 day run, and ethylene benzene having a low of approximately 0.75% at the beginning to approximately 1.0% at the end of the run.

Example 2

Run conditions for Example 2 were the same as Example 1 except that the polystyrene in toluene percentage was increased 10.3%. Styrene content in the effluent increased to 7.1%.

Example 3

Run conditions for Example 4 where the same as Example 1, except that Polystyrene 825E (HIPS) (91% styrene content) was used. After two days, the styrene content of the reactor effluent was 6.3% with a yield of 63%. The effluent from the reactor had the following makeup:

| Liquid Product | % |
|---|---|
| Styrene | 6.31 |
| Toluene | 91.15 |
| AMS | 0.33 |
| Stilbene | 0.07 |
| Benzene | 0.09 |
| Ethyl Benzene | 0.16 |
| Heavies/Unknown | 1.58 |

While there was only 6.3 wt % styrene in the reactor effluent, 825E contains 7 wt % rubber, meaning the actual styrene monomer content without the rubber would be approximately 6.8 wt %

While the foregoing is directed to embodiments of the present invention, other and further embodiments of the invention may be devised without departing from the basic scope thereof and the scope thereof is determined by the claims that follow.

What is claimed is:

1. A process for reclaiming styrene monomer from a waste plastic comprising:
   caustic treating a polymer stream, hydrotreating the polymer stream, or combinations thereof, wherein the polymer stream comprises polymers dissolved from the waste plastic; and
   depolymerizing the polymers dissolved from the waste plastic to form styrene monomer in a styrene monomer stream.

2. The process of claim 1, wherein the polymer stream is caustic treated before depolymerizing.

3. The process of claim 2, wherein the caustic treatment removes nitrile groups in acrylonitrile polymers in the polymer stream, and converts at least some of the nitrile groups to carboxylate groups.

4. The process of claim 2, wherein the caustic treating of the polymer stream comprises contacting the polymer stream with a caustic solution.

5. The process of claim 1, wherein the polymer stream is caustic treated and then hydrotreated before the depolymerizing.

6. The process of claim 1, wherein the polymer stream is hydrotreated before the depolymerizing.

7. The process of claim 6, wherein the hydrotreating removes halogens from the polymer stream.

8. The process of claim 1 further comprising:
   heating the polymer stream to a temperature below a temperature at which a solvent in the polymer stream flashes.

9. The process of claim 1 further comprising:
   cooling the styrene monomer stream by exchanging heat with the polymer stream in a preheater.

10. The process of claim 9, further comprising after the cooling of the styrene monomer stream, neutralizing the styrene monomer stream to a pH of 5 to 9.

11. The process of claim 10, wherein the neutralizing of the styrene monomer stream comprises combining a neutralizing stream with the styrene monomer stream.

12. The process of claim 11, wherein the neutralizing stream comprises a caustic or amine solution.

13. The process of claim 10, wherein after neutralizing the styrene monomer stream, the styrene monomer stream is fed to a compartment decanter, wherein hydrocarbons are separated from steam condensate and salts from neutralization.

14. The process of claim 1 further comprising:
wherein the step of depolymerizing polymers dissolved from the waste plastic to form styrene monomer is performed at a temperature of equal to or greater than 600° C.

15. The process of claim 14, wherein a residence time of the polymers dissolved from the waste plastic in the reactor is less than or equal to 1 minute.

16. The process of claim 14, wherein the reactor is an adiabatic fixed bed reactor, a fluidized bed reactor, a falling bed reactor, a tubular reactor, or a direct-fired tubular reactor.

17. The process of claim 14, wherein prior to the depolymerizing, the polymers dissolved from the waste plastic are heated to the depolymerization temperature.

18. The process of claim 17, wherein the polymers dissolved from the waste plastic are heated to the depolymerization temperature in less than 3 seconds.

* * * * *